United States Patent [19]

Barer et al.

[11] Patent Number: 4,725,542
[45] Date of Patent: Feb. 16, 1988

[54] PRODUCTION OF NYLON 6,6 SALT

[75] Inventors: Sol J. Barer, Fanwood; Peter C. Maxwell, New Providence; Jih-Han Hsieh, Parsippany, all of N.J.

[73] Assignee: Celgene Corporation, Warren, N.J.

[21] Appl. No.: 457,808

[22] Filed: Jan. 13, 1983

[51] Int. Cl.$^4$ .......... C12P 13/00; C12P 7/40; C12N 9/02; C12N 9/07
[52] U.S. Cl. .......... 435/128; 435/136; 435/142; 435/189; 435/190; 435/253; 435/261; 435/313
[58] Field of Search ........... 435/128, 136, 142, 189, 435/190, 253, 261, 313, 813, 877

[56] References Cited

U.S. PATENT DOCUMENTS

| | | | |
|---|---|---|---|
| 3,952,051 | 4/1976 | Ogawa et al. | 260/501.2 |
| 3,965,985 | 6/1976 | Hitzman | 435/101 |
| 4,156,630 | 5/1979 | Müller | 435/813 |
| 4,355,107 | 10/1982 | Maxwell | 435/877 |
| 4,411,991 | 10/1983 | Hirakawa et al. | 435/42 |

OTHER PUBLICATIONS

Morrison and Boyd, *Organic Chemistry*, 3rd ed., 1977, Allyn and Bacon, Inc., p. 1042.
Condensed Chemical Dictionary, 9th edition, revised by G. Hawley, Van Nostrand Reinhold Co., N.Y., 1977, p. 629.

*Primary Examiner*—Thomas G. Wiseman
*Assistant Examiner*—Robin Lyn Teskin
*Attorney, Agent, or Firm*—Depaoli & O'Brien

[57] ABSTRACT

This invention provides a process for producing nylon 6,6 salt which involves bioconversion of toluene to muconic acid in the presence of hexamethylenediamine to yield hexamethylenediamine muconate salt. Hydrogenation of this salt provides an aqueous solution of the desired hexamethylenediamine adipate salt.

13 Claims, No Drawings

PRODUCTION OF NYLON 6,6 SALT

BACKGROUND OF THE INVENTION

Adipic acid is an important commodity in the chemical industry, particularly for consumption as a comonomer in the synthesis of polymers. Adipic acid is obtained by oxidation of cyclohexane or cyclohexanol on a commercial scale.

Indicative of the volume of adipic acid directed to polymer production, in 1980 the market for nylon 6,6 was about 1.5 billion pounds. A monomer precursor for nylon 6,6 is a 50% aqueous solution of "nylon 6,6 salt", which is an ionic combination of adipic acid and hexamethylenediamine:

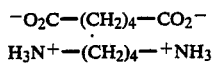

Hexamethylenediamine can be derived from adipic acid via amide and nitrile intermediates.

There is continuing research effort to develop new and improved processes for the production of commodity chemicals such as adipic acid and hexamethylenediamine.

One prospective method for synthesis of adipic acid is by the hydrogenation of muconic acid, which is a di-olefinically unsaturated adipic acid derivative:

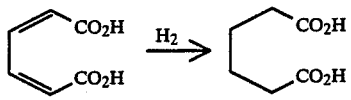

A potentially convenient source of muconic acid is by the microbiological oxidation of various hydrocarbon substrates. Microbiological oxidation of hydrocarbons is reviewed in Applied Microbiology, 9(5), 383(1961) and in "Advances in Enzymology", 27, 469–546(1965) by Interscience Publishers. The prospect of biotechnical methods for commercial scale production of commodity chemicals is under active investigation.

Accordingly, it is an object of this invention to provide a process for production of muconic acid by microbiological oxidation of a hydrocarbon substrate.

It is another object of this invention to provide a novel process for the production of nylon 6,6 salt which involves a microbiological fermentation step.

It is a further object of this invention to provide a process for production of adipic acid and hexamethylenediamine.

Other objects and advantages of the present invention shall become apparent from the accompanying description and examples.

DESCRIPTION OF THE INVENTION

One or more objects of the present invention are accomplished by the provision of a process for the production of hexamethylenediamine muconate salt which comprises (1) feeding toluene to an aqueous fermentation medium containing hexamethylenediamine and a microorganism strain capable of metabolizing toluene to muconic acid and having the following characteristics:

(a) possesses catechol 1,2-oxygenase enzyme with activity that is not inhibited in the presence of a low level of muconic acid in a growth medium;
(b) lacks active catechol 2,3-oxygenase enzyme;
(c) lacks active muconate lactonizing enzyme;
(d) cells are rod shaped, vigorously motile and polarly flagellated; and
(e) cells grow well on p-hydroxybenzoate;

and (2) separating the microorganism cells from the aqueous fermentation medium which contains hexamethylenediamine muconate salt product in solution.

In another embodiment, the present invention provides a process for the production of hexamethylenediamine adipate salt which comprises (1) feeding toluene to an aqueous fermentation medium containing hexamethylenediamine and a fluorescent Pseudomonas microorganism strain having the following characteristics:

(a) possesses catechol 1,2-oxygenase enzyme with activity that is not inhibited in the presence of a low level of muconic acid in a growth medium;
(b) lacks active catechol 2,3-oxygenase enzyme;
(c) lacks active muconate lactonizing enzyme;
(d) cells are rod shaped, vigorously motile and polarly flagellated; and
(e) cells grow well on p-hydroxybenzoate;

(2) separating the microorganism cells from the aqueous fermentation medium which contains hexamethylenediamine muconate salt in solution; and (3) subjecting the cell-free aqueous solution provided by step(2) to hydrogenation conditions to convert hexamethylenediamine muconate salt to hexamethylenediamine adipate salt.

In a further embodiment, the present invention provides a process for the production of hexamethylenediamine and hexamethylenediamine muconate salt which comprises (1) feeding toluene to an aqueous fermentation medium containing hexamethylenediamine and a microorganism strain capable of metabolizing toluene to muconic acid and having the following characteristics:

(a) possesses catechol 1,2-oxygenase enzyme with activity that is not inhibited in the presence of a low level of muconic acid in a growth medium;
(b) lacks active catechol 2,3-oxygenase enzyme;
(c) lacks active muconate lactonizing enzyme;
(d) cells are rod shaped, vigorously motile and polarly plagellated; and
(e) cells grow well on p-hydroxybenzoate;

(2) separating the microorganism cells from the aqueous fermentation medium which contains hexamethylenediamine muconate salt in solution; (3) recovering the hexamethylenediamine diamine muconate salt from at least a portion of the cell-free aqueous solution from step(2); (4) treating the muconate salt with ammonia under amide-dehydration conditions to form mucononitrile; and (5) subjecting the mucononitrile to hydrogenation conditions to convert the mucononitrile to hexamethylenediamine.

The term "nylon 6,6 salt" as employed herein refers to hexamethylenediamine adipate salt.

The term "HMDA" as employed herein refers to hexamethylenediamine.

The series of biochemical and chemical steps involved in the present invention process embodiments can be represented by the following flow diagram:

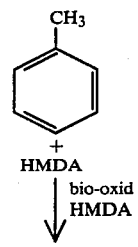

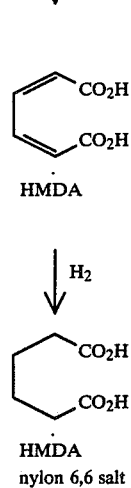

HMDA
nylon 6,6 salt

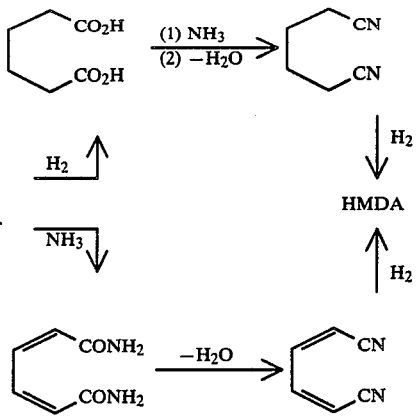

Toluene To Muconic Acid

No known naturally occurring microorganism population is suitable for the step(1) bio-oxidation of toluene to an accumulated quantity of muconic acid. Patent application Ser. No. 287,343, filed July 27, 1981, now U.S. Pat. No. 4,355,107, incorporated by reference, describes a process for the construction of novel microorganism strains which are adapted for toluene conversion to recoverable muconic acid.

The strain construction procedure involves (1) culturing microorganism species selectively to provide strain A1 which metabolizes toluene by the ortho pathway via catechol to muconic acid, and which subsequently metabolizes the resultant muconic acid via␤-ketoadipate to biomass and carbon dioxide; (2) continuously and selectively culturing strain A1 for rapid growth on toluene as the sole source of carbon to provide strain A2; (3) culturing strain A2 in selective enrichment cycles in a medium containing benzoate as the sole source of carbon and containing an antibiotic which kills only growing cells; (4) harvesting the strain A2 cells and diluting and culturing the cells in media containing a non-selective carbon source; (5) plating the strain A2 cells on a nutrient medium containing a limiting amount of a non-selective carbon source and excess benzoate; (6) isolating cells from single small colonies, and culturing the cell isolates and selecting a strain A3, wherein strain A3 converts toluene to muconic acid and lacks active muconate lactonizing enzyme.

The starting microorganism for the strain construction can be any organism capable of growth on toluene and possessing a catechol 1,2-oxygenase, e.g., a Pseudomonad. A variety of naturally occurring organisms have these traits including some members of the species Pseudomonas putida, Pseudomonas aeruginosa, Pseudomonas fluorescens; some members of the genera Azotobacter and Nocardia; and a number of unclassified fungi (both molds and yeasts).

Preferred constructed microorganisms are those that possess a novel combination of enzymes which include (1) dihydrodihydroxybenzoate dehydrogenase enzyme; and (2) catechol 1,2-oxygenase enzyme with activity that is not inhibited in the presence of less than about one gram/liter of muconic acid in a growth medium.

A novel strain of Pseudomonas putida Biotype A, constructed in accordance with Example II herein and having the above recited characteristics, has been deposited with the American Type Culture Collection and has been designated as ATCC No. 31,916.

Employing one of the constructed microorganisms described above for the production of muconic acid from toluene, the rate of toluene conversion typically is about 0.3–1.2 grams of muconic acid produced per dry weight gram of cells per hour. The conversion of toluene proceeds readily at a dry weight cell concentration of 1–3 grams per liter, with a resultant muconic acid production rate of 0.4–2 grams per liter per hour. Under optimal conditions, the muconic acid accumulation limit can vary between about 5–30 grams of muconic acid per liter of growth medium. The bioconversion normally is conducted at ambient temperatures up to about 35° C.

The production of muconic acid from toluene is sensitive to the level of growth carbon (catabolite repression), nutrient concentration (i.e., cell stability), muconic acid concentration (end product inhibition and repression) and toluene level and mass transfer rate to the fermentation broth (enzyme induction and growth inhibition).

As described in Example V, continuous production of muconic acid from toluene can be conducted in a chemostat using a mutant strain of Pseudomonas putida. Under nitrogen-limitation conditions, the mutant strain population is stabilized to over 20 residence times (i.e., without substantial reversion to the parent strain). Steady state muconic acid concentration of 10 mmoles at dilution rate of 0.20 hr$^{-1}$ and specific productivity of 0.29 g product/g cells/hr is achievable.

Consequentially, with the formation of muconic acid metabolite in step(1) of the invention process, the muconic acid is neutralized by and forms a salt with the hexamethylenediamine which is present in the fermentation medium.

Preferably, the hexamethylenediamine is introduced continuously or intermittently to the fermentation medium concurrently with muconic acid production in a quantity sufficient to neutralize the muconic acid without the presence of an excess of hexamethylenediamine.

The use of hexamethylenediamine as a neutralizing reagent has particular advantage for purposes of the step(1) bioconversion procedure. Maintenance of approximately neutral pH with hexamethylenediamine instead of a conventional alkaline reagent such as sodium hydroxide is significant ecologically in terms of byproduct waste stream accumulation and disposal. When sodium hydroxide is employed as a pH control reagent, the subsequent required treatment of the fermentation medium with an acid reagent such as sulfuric acid results in an accumulation of a sodium sulfate type of byproduct. Also, the use of hexamethylenediamine eliminates the cost of utilizing a conventional alkaline reagent.

As a further advantage, the hexamethylenediamine neutralizing reagent also constitutes an essential component of nylon 6,6 salt. As described hereinabove, the presence of hexamethylenediamine in the fermentation broth provides a hexamethylenediamine muconate salt product, which is convertible directly into hexamethylenediamine adipate (i.e., nylon 6,6 salt).

HMDA-muconate to HMDA-adipate

The HMDA-muconate salt in the cell-free aqueous fermentation broth provided by step(2) of the invention process is readily convertible into an aqueous solution of nylon 6,6 salt, by subjecting the fermentation broth to hydrogenation conditions.

Conventional hydrogenation conditions can be employed, such as the use of a heterogeneous catalyst component (e.g., a Group VIII metal on a carrier), and a 15-500 psi partial pressure of hydrogen in a hydrogenation reactor unit.

Alternatively, the HMDA-muconate salt can be precipitated from the fermentation broth by addition of a water-miscible organic solvent such as propanol, isopropanol, tetrahydrofuran, dimethylformamide, and the like. The solid HMDA-muconate salt precipitate can be recovered by filtration. The solid salt product can be slurried or dissolved in an aqueous or other medium for subsequent treatment.

The HMDA-muconate salt can also be isolated from the fermentation broth by other procedures such as reverse osmosis, crystallization, freeze crystallization, and the like.

HMDA-muconate to 2HMDA

A further advantage of the present invention process is that a mole of HMDA-muconate can be converted to two moles of HMDA, which in turn can be recycled to step(1) of the process.

As illustrated in the flow diagram above, conventional procedures can be employed to transform HMDA-muconate to HMDA-adipate; HMDA-muconate to HMDA and mucononitrile by ammonolysis in the presence of an amide-dehydration catalyst; and mucononitrile to hexamethylenediamine by hydrogenation. The resultant aqueous solution contains two moles of HMDA for each mole of HMDA-muconate originally present.

The following examples are further illustrative of the present invention. The components and specific ingredients are presented as being typical, and various modifications can be derived in view of the foregoing disclosure within the scope of the invention.

The basal salts media employed in the series have the compositions defined in Table I. The media have a pH of 6.0-7.2 (as controlled by HMDA addition), and the original microorganism used in the Examples is constructed from a natural isolate.

For cultivation, growth carbon sources such as acetate and succinate are added aseptically prior to inoculation. Incubation conditions are in 250 ml shake flasks. Shaking is in a rotary shaker with temperature controlled at about 30° C.

Growth is typically measured by determining the turbidity of the cell suspension in a Klett-Summerson Colorimeter using the #66 red filter. One Klett unit is equivalent to about $3 \times 10^6$ cells per ml or 17.5 mg wet weight per liter or 3.5 mg dry weight per liter.

Cultures are stored under liquid nitrogen.

EXAMPLE I

This Example illustrates the construction of a strain of microorganism which oxidizes toluene via the ortho ($\beta$-ketoadipate) pathway.

A series of mutants which metabolize toluene through the ortho pathway is constructed by first blocking the meta pathway and then isolating phenotypic revertants which have reacquired the ability to grow on benzoate. Strains possessing a meta pathway block are isolated after penicillin plus D-cycloserine enrichment for organisms which fail to grow on benzoate. Some isolates are then spotted into agar plates and incubated in the presence of toluene. Virtually all isolates revert to growth on toluene. The plates are sprayed with 10 mM catechol and approximately 25% of the revertants are found not to produce 2-hydroxymuconic semialdehyde. None of the colorless revertants are found to possess an active catechol 2,3-oxygenase following induction with toluene.

It has been shown by Worsey and Williams, J. Bacteriol. 130, 1149 (1977) that growth on benzoate tends to cure a population of its TOL plasmid because the ortho pathway supports a higher growth rate. Since toluate can only be metabolized via the meta pathway, an alternative way to cure a population of its TOL plasmid is to use the penicillin plus D-cycloserine procedure to enrich for cells unable to grow on toluate.

Both these techniques are used in succession followed by counter-selection for growth on toluene. A strain designated MW 1200 is first cultured on toluene. A small portion (0.05 ml) of this culture is transferred to 50 ml of benzoate medium. After growth on benzoate the cells are transferred to toluate and incubated for approximately one hour. Penicillin and D-cycloserine are then added as described above and the incubation is continued for four to six hours. Cells are harvested, washed and transferred to a toluene containing medium.

After growth on toluene the cells are plated on benzoate agar and incubated for 48 hours, and a number of large colonies and a few small colonies are formed.

After spraying with catechol it is found that all of the small colonies turn yellow (indicating the presence of the meta pathway) but none of the large colonies do. Large colonies are picked and cultured and it is found that following growth on toluene, these strains contain no functional 2,3-oxygenase but are fully induced for the 1,2-oxygenase. These strains metabolized toluene by the ortho pathway. One isolate, designated MW 1210, is employed in Example II.

EXAMPLE II

This Example illustrates the construction of a *Pseudomonas putida* Biotype A strain ATCC No. 31,916 type of mutant strain.

Strain MW 1210 of Example I is subjected to continuous cultivation with toluene as the sole source of carbon. Initially a dilution rate of 0.15 hours$^{-1}$ is employed. After the culture has stabilized, the dilution rate is increased successively to 0.25 hour$^{-1}$, 1, 0.34 hour$^{-1}$, and 0.46 hour$-1$. An isolate is made from the cells which dominates the culture at this latter dilution rate. This strain is then used to construct a strain which accumulates muconic acid to greater than one gram per liter.

The above strain is cultured overnight in liquid medium on toluene as the sole source of carbon, then benzoate is added to a level of 5 mM and the incubation is continued for approximately 1 hour. Penicillin G and D-cycloserine are added at concentrations of 12 and 0.1 mg/ml respectively. The antibiotic incubation is continued for approximately 5 hours. The cells are then harvested by centrifugation and washed twice with sterile de-ionized water. An aliquot of these cells is transferred to fresh medium containing 0.5 mM p-hydrobenzoate as a sole source of carbon, and the medium is incubated overnight. The procedure is repeated starting with induction with benzoate.

After 6 cycles those cells present in the culture after overnight growth on p-hydroxybenzoate are diluted and plated on an agar medium containing 0.5 mM succinate and 5.0 mM benzoate as sole sources of carbon. After 36 hours incubation the plate shows a mixture of large and small colonies. Cells from a number of small colonies are cultured in liquid medium, induced with toluene and tested for their ability to accumulate muconic acid. Isolate strains which accumulate muconic acid are identified.

EXAMPLE III

This Example illustrates the preparation of nylon 6,6 salt in accordance with the present invention.

Inoculum Preparation

A *Pseudomonas putida* Biotype A strain ATCC No. 31,916 culture (regular "NO" medium aqueous culture in polypropylene vial stored in liquid nitrogen) is thawed and transferred (1~1.5 ml) to a 250 ml shake flask containing 50 ml of regular "NO" medium (Table I) with 5mM of sodium succinate as a growth carbon source, and incubated at 30° C., 250 RPM for nine to eighteen hours to an optical density of 50~60 klett units.

The 50 ml culture is then transferred to a 2.5 liter shake flask containing one liter of modified "NO" medium (Table I) with 20 mM of sodium acetate as a carbon source. Also included in the shake flask are three polypropylene vials containing toluene, which are adapted to permit slow passage of the toluene from the vials into the culture medium as an inducer.

The shake flask medium is incubated at 30° C. and 250 RPM for nine to eighteen hours to an optical density of 60~90 klett units. The resultant culture is then inoculated to a 16 liter steam sterilizable fermentor (New Brunswick Scientific, Model SF 116) containing 11 liters of modified "NO" medium with 20 mM of sodium acetate to start fermentation.

Enzyme Induction

After the inoculation, toluene is supplied to the fermentor medium in vapor phase via air (filter sterilized), stripping at an air-toluene vapor rate of 125 cc/min. The fermentation temperature is controlled at 30° C., and the pH at 6.9 with 35% (w/v) hexamethylenediamine aqueous solution.

Air is sparged through the fermentor medium at 5.0 liter/min rate of aeration (approx. 0.5 VVM). The dissolved oxygen in the medium is at 30–100% saturation. Pluronic L61 polyol (BASF) is used as an antifoam agent.

Product Formation

As the turbidity of the fermentation medium reaches 60~90 klett units (usually about 6~9 hours after inoculation), an aqueous solution containing 10 wt % acetic acid and 1.38 wt % (NH$_4$)$_2$SO$_4$ is added to the fermentor medium at a rate of 0.4 ml/min. The air-toluene vapor rate is increased to 250 cc/min, and then increased to 500 cc/min as the turbidity reaches 250 klett units. The pH is controlled by addition of hexamethylenediamine.

The "fed-batch" mode of fermentation is continued for 24 hours, and the hexamethylenediamine muconate salt concentration reaches 30 g/l at a cell concentration of 1.8 g dry weight/l.

Cell Separation

The culture broth is filtered to remove cells with a Romicon ® hollow tube "cross-flow" ultrafilter which has a polysulfone type ultrafiltration membrane (PM-100 molecular weight cut off 100,000). The ultrafiltration module has a total membrane area of 1.1 ft$^2$ (50 tubes in a 1.0"×25" cylindrical polypropylene cartridge). The fermentation broth with cells is pumped (Micro gear pump) to the ultrafilter at an inlet pressure of 10 psig and at a flux rate of 68 ml/min ft$^2$.

Hydrogenation

To the cell free aqueous fermentation solution containing 3.0 wt % hexamethylenediamine muconate salt is added 0.5 wt % of Pd/C (10% Pd on C) catalyst. The slurry is charged into a Parr hydrogenator and hydrogenated at 22° C. and 50 psig hydrogen partial pressure. Based on UV measurement at 257 nm and hydrogen consumption, the unsaturated muconate in the salt solution is quantitatively converted to the saturated diacid at an initial rate of 0.92 ×10$^{-5}$ g mole/cm$^3$ solution min. The resulting hydrogenated salt solution is then concentrated to a 50 wt % hexamethylenediamine adipate (Nylon 6,6 salt) solution by evaporation.

Ammonolysis/Dehydration/Hydrogenation

HMDA·muconate salt (M.P. 236° C.) is admixed with 2 weight percent of calcium phosphate dehydration catalyst in a reactor, and the reactor is charged with gaseous ammonia in a molar ratio of 5:1 of ammonia to HMDA·muconate salt.

The reaction mixture is heated to about 250° C., at which temperature the reaction mixture is in a molten state. After about one hour of heating, the resultant HMDA/mucononitrile product mixture is distilled to remove ammonia and water.

The residual crude HMDA/mucononitrile product is dissolved in toluene, and the solution is admixed with 0.5 weight percent nickel-tungsten hydrogenation catalyst, based on the weight of mucononitrile, in a hydrogenation reactor system.

The hydrogenation is conducted at a temperature of 130° C. and a hydrogen pressure of about 2000 psi. HMDA product is recovered overhead as an azeotrope with water. The HMDA is purified further by fractional distillation, and then recycled in the overall process of toluene/HMDA conversion to nylon 6,6 salt.

EXAMPLE IV

The inoculum preparation, enzyme induction procedures and product formation are the same as Example III, except that after 24 hours of fermentation the addition of the 10 wt % acetic acid and 1.38 wt % $(NH_4)_2SO_4$ solution is stopped. Additional 18 hours of fermentation is performed with air-toluene vapor sparging at 500 cc/min. The hexamethylenediamine muconate salt concentration reaches 39 g/l at a cell concentration of 2.3 g dry weight/l.

The fermentation broth is filtered to remove cells with the Romicon® ultrafilter. The HMDA-muconate salt is precipitated by adding 50% (v/v) isopropyl alcohol to the cell-free fermentation aqueous solution. The precipitated hexamethylenediamine muconate salt is filtered and recovered (approximately 50% recovery in single pass).

The recovered and dried salt is resuspended (3 wt %) in 25 vol. % methanol deionized water solution, and hydrogenated in the presence of 0.5 wt % Pd/C (10% Pd on C) catalyst in a Parr hydrogenator at 22° C. and 50 psig hydrogen partial pressure. The muconate is quantitatively hydrogenated at an initial rate of $5.5 \times 10^{-5}$ g mole/cm$^3$ solution/min. The resulting hydrogenated solution is then concentrated to a 50 wt % hexamethylenediamine adipate (Nylon 6,6 salt) solution by evaporation.

EXAMPLE V

The inoculum preparation, enzyme induction procedures and product formation are the same as Example III, except that after 20 hours of "fed-batch" fermentation (at a HMDA-muconate salt concentration of 22 g/l and cell concentration of 2.1 g/l) the fermentation is converted to a continuous operation with a cell recycle mode.

To operate the continuous/cell recycle system, fresh membrane sterilized LN-1 medium (Table I) is pumped (FMI piston pump) into the fermentor at a rate of 60 ml/min. The fermentation broth is pumped from the fermentor with an internal circulation pump (Micor gear pump) to two parallel Romicon® hollow tube ultrafilters with a polysulfone type ultrafiltration membrane (PM-100, molecular weight cut off 100,000). Total membrane area is 2.2 ft$^2$. Each filter contains 50 tubes in a 1.0"×25" cylindrical polypropylene cartridge. The fermentation broth with cells is "crossflow" filtered by the ultrafilter and controlled at a permeate (clean, cell-free product stream) rate of 60 cc/min with a Dwyer flowmeter (needle valve). The fermentation broth level in the fermentor is controlled at 11 liter working volume by a New Brunswick level controller which actuates the fresh medium feed pump.

The fermentation broth with cells is continuously circulated "through" the ultrafilter at an internal circulation rate of 3.0 to 4.5/l min and a pressure drop of 5 to 10 psig across the ultrafiltration membrane. After initial decrease, the product concentration in the cell free permeate stream is maintained at 6.5 g/l. The air-toluene vapor rate is increased to 1000 cc/min. The continuous/cell recycle run is operated for six hours without cell purge.

The cell concentration is increased to 3.0 g/l (equivalent to 850 klett units). Under these conditions, a reactor productivity of 2.0 g of HMDA-muconate salt/l/hr is achieved.

TABLE I

| Chemicals | MEDIUM COMPOSITIONS | |
|---|---|---|
| | (g/l) | (mM) |
| A. Regular "NO" Medium | | |
| $Na_2HPO_4$ | 7.1 | 50 |
| $KH_2PO_4$ | 13.6 | 100 |
| $(NH_4)_2SO_4$ | 2.25 | 17 |
| $MgSO_4.7H_2O$ | 0.246 | 1 |
| $CaCl_2$ | 0.0111 | 0.1 |
| $FeSO_4.7H_2O$ | 0.00278 | 0.01 |
| With appropriate growth carbon source in deionized water. | | |
| B. Modified "NO" Medium | | |
| $Na_2HPO_4$ | 7.1 | 50 |
| $KH_2PO_4$ | 13.6 | 100 |
| $(NH_4)_2SO_4$ | 0.281 | 2.1 |
| $MgSO_4.7H_2O$ | 0.738 | 3 |
| $CaCl_2$ | 0.0222 | 0.2 |
| $FeSO_4.7H_2O$ | 0.00834 | 0.03 |
| With appropriate growth carbon source in deionized water. | | |
| C. LN-1 Medium | | |
| $H_3PO_4$ (86% w/w) | 14.5 | 150 |
| NaOH | 4.0 | 100 |
| KOH | 5.6 | 100 |
| $MgSO_4.7H_2O$ | 0.738 | 3.0 |
| $CaCl_2$ | 0.0222 | 0.2 |
| $FeSO_4.7H_2O$ | 0.00834 | 0.03 |
| $(NH_4)_2SO_4$ | 0.0185 | 0.14 |
| Acetic Acid | 0.131 | 2.2 |
| In deionized water. | | |

What is claimed is:

1. A process for the production of hexamethylenediamine muconate salt which comprises (1) feeding toluene to an aqueous fermentation medium containing hexamethylenediamine and a microorganism strain which metabolizes the toluene to muconic acid and has the following characteristics:
    (a) possesses catechol 1,2-oxygenase enzyme with activity that is not inhibited in the presence of a low level of muconic acid in a growth medium;
    (b) lacks active catechol 2,3-oxygenase enzyme;
    (c) lacks active muconate lactonizing enzyme;
    (d) cells are rod shaped, vigorously motile and polarly flagellated; and
    (e) cells grow well on p-hydroxybenzoate;
and (2) separating the microorganism cells from the aqueous fermentation medium which contains hexamethylenediamine muconate salt product in solution.

2. A process in accordance with claim 1 wherein the microorganism is a substantially biologically pure culture of a *Pseudomonas putida* Biotype A strain which converts toluene to muconic acid at a rate between about 30–1200 milligrams of muconic acid produced per dry weight gram of cells per hour, with an accumulation of greater than about five grams of muconic acid per liter of aqueous medium.

3. A process in accordance with claim 1 wherein the microorganism is ATCC No. 31,916 strain of *Pseudomonas putida* Biotype A.

4. A process in accordance with claim 1 wherein toluene is added to the aqueous medium as a vapor phase component of a molecular oxygen-containing stream.

5. A process in accordance with claim 1 wherein the aqueous medium contains a carbon source selected from succinate, acetate, glucose, lysine, gluconate and 2-keto-gluconate.

6. A process in accordance with claim 1 wherein the hexamethylenediamine is supplied continuously to the fermentation medium in a quantity sufficient to neutralize and form a salt with the muconic acid as it is formed by the bioconversion of toluene in step(1).

7. A process in accordance with claim 1 wherein the microorganism cells are separated from the fermentation medium in step (2) by crossflow ultrafiltration.

8. A process in accordance with claim 1 wherein a water-miscible organic solvent is added to the cell-free aqueous solution from step (2) to precipitate the hexamethylenediamine muconate salt as a recoverable solid product.

9. A process for the production of hexamethylenediamine adipate salt which comprises (1) feeding toluene to an aqueous fermentation medium containing hexamethylenediamine and a microorganism strain which metabolizes the toluene to muconic acid and has the following characteristics:
(a) possesses catechol 1,2-oxygenase enzyme with activity that is not inhibited in the presence of a low level of muconic acid in a growth medium;
(b) lacks active catechol 2,3-oxygenase enzyme;
(c) lacks active muconate lactonizing enzyme;
(d) cells are rod shaped, vigorously motile and polarly flagellated; and
(e) cells grow well on p-hydroxybenzoate;
(2) separating the microorganism cells from the aqueous fermentation medium which contains hexamethylenediamine muconate salt in solution; and (3) subjecting the cell-free aqueous solution provided by step (2) to catalytic hydrogenation conditions to convert hexamethylenediamine muconate salt to hexamethylenediamine adipate salt.

10. A process in accordance with claim 9 wherein the microorganism is ATCC No. 31,916 strain of *Pseudomonas putida* Biotype A.

11. A process in accordance with claim 9 wherein the hexamethylenediamine is supplied continuously to the fermentation medium in a quantity sufficient to neutralize and form a salt with the muconic acid as it is formed by the bioconversion of toluene in step (1).

12. A process for the production of hexamethylenediamine and hexamethylenediamine muconate salt which comprises (1) feeding toluene to an aqueous fermentation medium containing hexamethylenediamine and a microorganism strain which metabolizes the toluene to muconic acid and has the following characteristics:
(a) possesses catechol 1,2-oxygenase enzyme with activity that is not inhibited in the presence of a low level of muconic acid in a growth medium;
(b) lacks active catechol 2,3-oxygenase enzyme;
(c) lacks active muconate lactonizing enzyme;
(d) cells are rod shaped, vigorously motile and polarly flatellated; and
(e) cells grow well on p-hydroxybenzoate;
(2) separating the microorganism cells from the aqueous fermentation medium which contains hexamethylenediamine muconate salt in solution; (3) recovering the hexamethylenediamine muconate salt from a portion of the cell-free aqueous solution provided by step (2); (4) treating the recovered hexamethylenediamine muconate salt from step (3) with ammonia under amide-dehydration conditions to form muconitrile; and (5) subjecting the muconitrile to catalytic hydrogenation conditions to convert the mucononitrile to hexamethylenediamine.

13. A process in accordance with claim 12 wherein the hexamethylenediamine product from step (5) is recycled to step(1).

* * * * *